(12) United States Patent
Vaillancourt

(10) Patent No.: US 6,607,519 B2
(45) Date of Patent: Aug. 19, 2003

(54) FLUID ABSORBER FOR A SUCTION TUBE SET

(76) Inventor: Vincent L. Vaillancourt, 14 Bunyan Dr., Livingston, NJ (US) 07039

( * ) Notice: Subject to any disclaimer, the term of this patent is extended or adjusted under 35 U.S.C. 154(b) by 0 days.

(21) Appl. No.: 09/764,907

(22) Filed: Jan. 18, 2001

(65) Prior Publication Data

US 2001/0012931 A1 Aug. 9, 2001

Related U.S. Application Data

(62) Division of application No. 09/326,269, filed on Jun. 7, 1999, now Pat. No. 6,254,590.

(51) Int. Cl.[7] ............................................... A61M 1/00
(52) U.S. Cl. ....................................... 604/540; 604/297
(58) Field of Search ............................... 604/73, 82–85, 604/2, 289, 290, 294, 297, 313, 317, 319, 327, 374, 378, 379, 540, 541–544; 606/107; 128/205.12, 205.27–206.19

(56) References Cited

U.S. PATENT DOCUMENTS

| 3,848,603 | A | * | 11/1974 | Throner | 604/247 |
| 4,813,931 | A | * | 3/1989 | Hauze | 600/573 |
| 5,000,192 | A | * | 3/1991 | Sealfon | 600/573 |
| 5,330,426 | A | * | 7/1994 | Kriesel et al. | 604/82 |
| 6,290,685 | B1 | * | 9/2001 | Insley et al. | 604/317 |

* cited by examiner

Primary Examiner—Brian L. Casler
Assistant Examiner—Catherine Serke
(74) Attorney, Agent, or Firm—Francis C. Hand; Carella, Byrne et al.

(57) ABSTRACT

The suction tube set employs a compressed cellulosic sponge mass as a fluid absorber in the suction line for absorbing an amount of fluid, for example 1.5 cc, without any significant increase in resistance to air flow. The compressed sponge mass is secured in place within a tubular housing of the suction tube set with a gap formed between each end of the sponge mass and an end cap of the housing to avoid blockage of air flow.

17 Claims, 1 Drawing Sheet

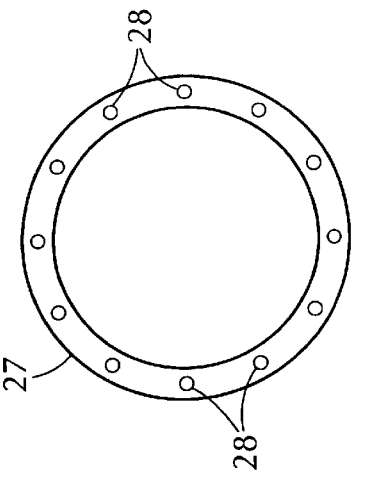
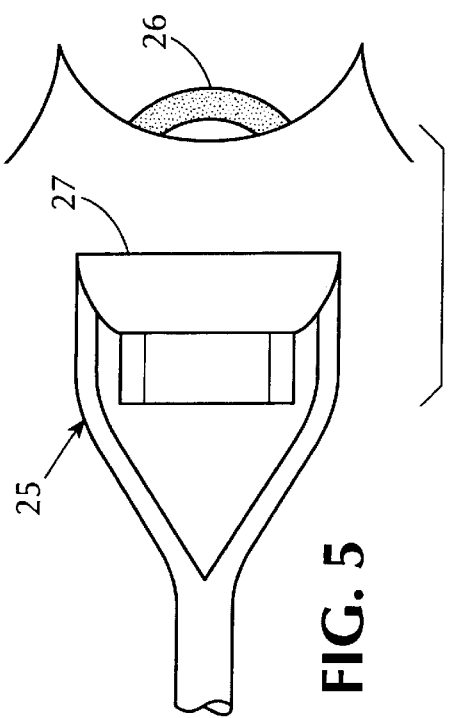
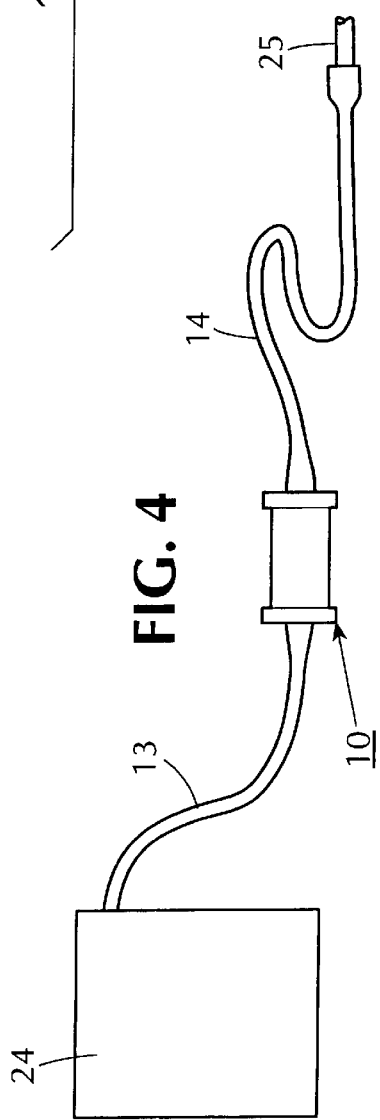
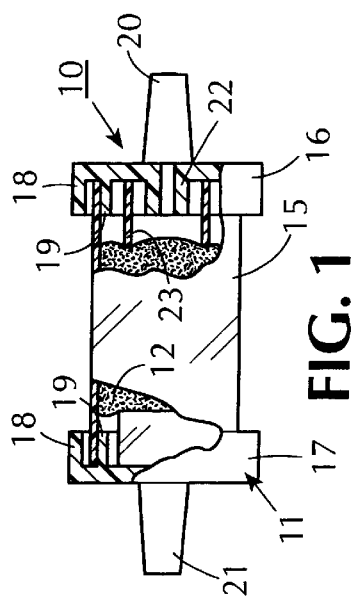
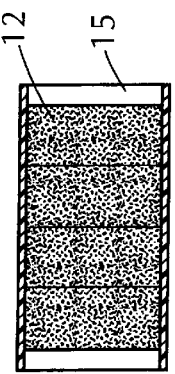

FLUID ABSORBER FOR A SUCTION TUBE SET

This application is a division of Ser. No. 09/326,269, filed Jun. 7, 1999 now U.S. Pat. No. 6,254,590B1.

This invention relates to a fluid absorber for a suction tube set. More particularly, this invention relates to a fluid absorber for a suction tube set for use in laser eye surgery.

As is known, various types of devices and equipment have been utilized in surgical procedures performed on an eyeball and particularly for photoretractive keratectomy laser surgery. During such procedures, a weak laser beam is used to remove tiny layers of tissue and to reshape the cornea to improve sight. Typically, photoretractive keratectomy is accomplished by an excimer laser beam that ablates away corneal tissue in a photodecomposition process. Before this occurs, a flap of the epithelium of the cornea is surgically removed to expose Bowman's layer on the anterior surface of the stroma. The excimer laser beam is then used for laser ablation at Bowman's layer. The laser beam is also used to remove corneal tissue to varying depths as necessary for re-contouring the anterior stroma. Afterward, the epithelium flap is repositioned to rapidly regrow and resurface the contoured area.

In order to stabilize an eyeball for purposes of such a surgical laser operation, it has been known to fix the eyeball in place using a suction device. This allows a surgeon to operate on the eyeball without the risk that the eyeball may move during the operation.

One known device for stabilizing an eyeball and for effecting removal of an epithelium flap is an automated disposable keratome sold by LaserSight Technologies, Inc. of Winter Park, Fla. This instrument provides a ring which is to be placed on the eyeball as well as a keratome for slicing a flap in the epithelium of the eyeball. Once the ring is in place with suction on, the keratome can be operated by a surgeon to cut the flap. High suction is generally required briefly to raise the LOP (intraocular pressure) and keep the eye rigid so that a clean cut can be made. However, there is a danger involved with such instruments if there is a loss of suction during this cutting time. Accordingly, the instrument is provided with an alarm that warns a surgeon instantly if suction is lost.

Studies have shown that the IOP rises to over 99 mmHg at maximum suction, with the estimated actual IOP during maximum suction being as high as 130 or 140 mmHg. However, prolonged exposure to this level of IOP creates a potential for damage to delicate retinal structures. Thus, in order to preclude damage, the time of exposure to high vacuum is limited to an absolute minimum.

Thus, with the suction ring in place and the vacuum set at 5 inches of mercury (Hg), the patient's IOP rises to the 30–35 mmHg range. This relatively safe level of vacuum is enough to hold the ring in place but not enough to produce a good cut. So when the surgeon activates the keratome, the vacuum rises immediately to 24 inches of mercury, pushing the IOP high enough for a good cut. However, the high vacuum lasts only for the 2 to 3 seconds required for the keratome to go forward across the ring. When the keratome goes back, the vacuum drops down again to 5 inches Hg, enough to hold the ring in place but not enough to endanger the retina and optic nerve.

Another problem which arises during an eye operation of the above type is due to the fact that tearing of the eyeball usually occurs so that fluid, i.e. salt water, is drawn into the suction ring and eventually into the vacuum pump. Should fluid begin to enter the vacuum pump, the pump can cease to draw a vacuum so that the eyeball is no longer locked in place. This is particularly the case where the pump retains fluid from a succession of eye operations.

In order to prevent fluids from migrating into the vacuum pump, fluid traps have been incorporated in the suction line between the vacuum pump and eyeball-engaging ring. That is to say, the line from the ring terminates in a vertically disposed trap to deliver fluid into the trap while a second line extends from the trap to the vacuum pump in order to conduct a vacuum force from the vacuum pump. Typically, the two lines are sealed relative to the interior of the trap so that a "reservoir" of fluid can be accumulated within the trap while an air space is provided above the "reservoir" of fluid to conduct an air flow therethrough. One of the problems with such a trap is that the trap must be maintained vertical as the trap operates under gravity. Accordingly, care must be taken to ensure that the trap does not turn upside down, as otherwise, fluid would immediately pass into the vacuum pump thereby rendering the pump inoperative.

It has also been known to place filters in the suction tube lines in order to prevent fluid coming from an eyeball to pass onto the vacuum pump. However, one problem associated with this technique is that as the eyeball side of the filter become filled with fluid, the resistance in the line to air flow increases. Thus, instead of the vacuum rising to 24 inches of mercury at the eyeball, a smaller vacuum force is generated at the ring-eyeball interface with the risk that a good cut in the epithelium may become compromised.

Another problem which may arise during an operation is that which is associated with a slight movement of the ring from the eyeball through accident or inadvertence which may cause a slight break in the vacuum due to a separation between the ring and the eyeball. Should this occur, an alarm would be sounded or visually indicated to the surgeon so that the ring may be reoriented and re-attached to the eyeball. However, if a filter has been provided in the suction line which has become filled with fluid on the eyeball side, the recovery time for the reengaging the ring with the eyeball is prolonged. In such a case, an eyeball movement can occur.

Accordingly, it is an object of the invention to reduce the risk of interrupting a photoretractive keratectomy laser operation due to a loss of vacuum caused by an accumulation of fluid in a vacuum pump.

It is another object of the invention to preclude an accumulation of fluid in a vacuum pump for instruments used in photoretractive keratectomy laser surgery.

It is another object of the invention to be able to trap fluid in a suction line set for a keratome without significantly increasing the resistance to air flow in the suction line.

Briefly, the invention provides a fluid absorber for a suction tube set for a keratome wherein the fluid absorber comprises a hollow housing for connection at one side to a vacuum pump and for connection at an opposite side to the keratome and a formed absorbent mass in the housing for absorbing fluid emanating from an eyeball without increasing the resistance to air flow at saturation by more than 3 inches of mercury. Typically, the absorbent mass is a cellulosic sponge mass.

In addition, the housing has a cap at each end with a spigot to receive either a suction tube or an inlet tube as the case may be. In addition, the fluid absorber includes a pair of spacer tubes, each of which is located between the sponge mass and the respective cap. These spacer tubes serve to space the sponge mass away from the spigot openings in the end caps in order to avoid clogging of the spigots. In addition, the spacer tubes serve to compress the sponge mass therebetween. This compression not only expands the sponge mass radially to engage against the inner diameter of the housing and close any space therebetween but also eliminates any through passage through the cells of the sponge mass from one end to the other.

In another embodiment, the sponge mass may be fixedly secured to the housing, for example by means of an adhesive at each end thereof, in order to prevent sliding of the sponge mass within the housing under a suction force of the vacuum pump.

The invention also provides a suction tube set which is comprised of the fluid absorber, a suction tube connected to one end of the housing of the fluid absorber for drawing a vacuum force within the housing and an inlet tube connected to and extending from an opposite end of the housing of the fluid absorber for conveying a vacuum force therethrough.

The suction tube set is connected to and between an eyepiece for fitting against an eyeball and a vacuum pump for drawing a vacuum at the eyepiece-eyeball junction. For example, the eyepiece may be the ring of an automated disposable keratome as sold by LaserSight Technologies Inc. of Winter Park, Fla. This ring is sized to engage an eyeball and has a plurality of ports for communicating with a passageway in the inlet tube.

The absorbent mass is particularly characterized in being able to absorb fluid without increasing the resistance to air flow by no more than 2 inches to 5 inches of mercury (Hg). The amount of fluid which is absorbed by the absorbent mass is based upon the expected amount of fluid which would be generated during an operation and by the amount of resistance created by a fluid-filled mass. That is to say, the absorbent mass is characterized in being able to absorb the amount of fluid expected to be generated during an operation without significantly increasing the resistance to air flow through the absorbent mass.

The purpose of forming a gap between the caps of the housing and the sponge mass is to avoid the sponge covering over the apertures of the respective caps which communicate with the suction line, as otherwise, the resistance to air flow could increase significantly thereby giving a false high value at the vacuum pump to a surgeon that the eyeball to which the eyepiece is locked may have become released and may have moved. In addition, a significant increase in air flow resistance would significantly increase the response time should vacuum be lost at the eyeball-eyepiece junction. This would also negate a safety pressure differential system at the vacuum pump which would notify the surgeon that vacuum has been lost.

Where the absorbent mass is a cellulosic sponge mass, it has been known to manufacture such sponges with an anti-bacterial agent in order to prevent the growth of mold and the like. In accordance with the invention, the cellulosic sponge mass is compressed to squeeze out the antibacterial agent. Further, compression of the sponge mass reduces the chance that there may be a continuous passage through the sponge mass for a flow of fluid. Typically, the sponge mass can be gamma sterilized to achieve a sterile product.

Further, it has been found that compression of the cellulosic sponge mass has little effect on the air flow resistance through the sponge mass.

Typically, the cellulosic sponge mass is hydrophillic and is commercially available under the trademark OCELLO and is sold by the 3M Company. Other types of sponge material may be polyurethane, hydrophillic polyethylene and polypropylene.

These and other objects and advantages of the invention will become more apparent from the following detailed description taking in conjunction with the accompanying drawings wherein:

FIG. 1 illustrates a broken view of the fluid absorber constructed in accordance with the invention;

FIG. 2 illustrates a cross-sectional view of the absorbent mass within the housing of the fluid absorber;

FIG. 3 illustrates an exploded view of the fluid absorber of FIG. 1;

FIG. 4 illustrates a schematic view of the suction tube set incorporating the fluid absorber and connected to an eyepiece at one end and to a vacuum pump at an opposite end;

FIG. 5 illustrates a perspective view of the eyepiece; and

FIG. 6 illustrates an end view of the eyepiece.

Referring to FIG. 1, the fluid absorber 10 is comprised of a hollowed housing 11 of tubular shape and a formed absorbent mass, such as a compressed cellulosic sponge mass 12 in the housing 11 for absorbing a fluid volume. As shown in FIG. 4, a suction tube 13 is connected to one end of the fluid absorber 10 for drawing a vacuum force within the housing 11 and an inlet tube 14 is connected to and extends from an opposite end of the fluid absorber 10 for conveying a vacuum force theretrough. The resulting suction tube set typically has a length of about 7 feet and is intended to be disposed of after a single use.

Referring to FIGS. 1 and 2 the housing 11 is constructed of an open end tube or barrel 15, for example, of clear, plastic material. By way of example, the barrel 15 has an inside diameter of 0.730 inches and a length of 1.5 inches.

As shown in FIGS. 1 and 3, the housing 11 also has an end cap 16 secured to one end of the barrel 15 and a second end cap 17 secured to the barrel 15 at the opposite end. Each end cap 16, 17 includes an outer rim 18 and an inner rim 19 to define a circumferential recess into which the barrel 15 fits. In addition, each end cap 16, 17 has a coaxial spigot 20, 21 extending on an opposite side from the rims 18, 19. Each end cap 16, 17 also has a hollow stem 22 facing inwardly of the barrel 15 which is of axial extent equal to the axial length of the inner rim 19 of the end cap 17.

Each end cap 16, 17 is sized so that the barrel 15 is slidably mounted on the outside diameter of the inner rim 19 of each. A suitable adhesive is also provided to secure each end cap 16, 17 to the surface of the barrel 15. By way of example, the adhesive may be a Loctite U.V. adhesive 3311-300 cP.

The spigot 20, 21 of each end cap 16, 17 is slightly tapered in a conventional manner to receive the respective tube 13, 14, as indicated in FIG. 4.

The sponge mass 12 is disposed within the barrel 15. In addition, a pair of spacer tubes 23 are disposed within the housing 11 with each tube 23 being disposed between the sponge mass 12 and a respective end cap 16, 17. During assembly, the sponge mass 12 is first placed within the barrel 15 as indicated in FIG. 2. Thereafter, as indicated in FIG. 3, a pair of spacer tubes 23 and the end caps 16, 17 are moved into and over the ends of the barrel 15. During this time, the spacer tubes 23 compress the sponge mass 12. As a result, the sponge mass 12 is longitudinally compressed while being radially expanded against the inner periphery of the barrel 15. The result is that any through passageway through the sponge mass 12 is broken up and eliminated and, at the same time, the sponge mass 12 is sealed against the inner periphery of the barrel 15 so that there are no pathways formed between the sponge mass 12 and the barrel 15.

The sponge mass 12 is formed, for example, by four coaxially disposed sections of sponge material which are compressed when assembled into the barrel 15.

The fluid absorber 10 in the suction tube set serves to absorb fluid (tears) passing to the absorber without increasing the resistances to air flow at saturation by more than 3 inches Hg.

Once assembled, the fluid absorber 10 is fitted with the suction tube 13 and inlet tube 14. The suction tube 13 may also be fitted with a connector of conventional structure, such as a Colder-DSM-2202, for connection to a vacuum pump 24 (see FIG. 4) in a conventional manner. In addition, the inlet tube 14 is connected to a keratome instrument 25.

Typically, the suction tube 13 is made of polyvinylchloride having dimensions of ¼"×⅛"×4". The inlet tube 14 is similarly made of polyvinylchloride with dimensions of ³⁄₁₆"×⅛"×84". The overall length of the two tubes 13, 14 is seven feet.

The sponge pieces employed within the housing 11 each have an initial uncompressed thickness of ⅝" and an outside diameter of ¾". In the compressed state, the axial length of the sponge mass 12 is slightly less than the axial length of the barrel 15 i.e. slightly less than 1.5". Thus, the four sponge pieces are reduced from an overall length of 2.5" to about half of that length.

Referring to FIG. 5, the keratome 25 is constructed, as is known, for fitting against an eyeball 26 and is typically provided with an end ring 27 of curved contour having a plurality of circumferentially disposed ports 28 through which air can be drawn. (See FIG. 6). These ports 28 are thus in communication with a passageway in the inlet line 14.

When a surgeon is to operate on the eyeball of a patient, the end ring 27 of the eyepiece 25 is brought into contact with the eyeball 26 and vacuum drawn on the eyepiece 25 so that the suction force effected through the ports 28 in the end ring 27 of the eyepiece 25 locks the eyeball 26 and end ring 27 together. Thus, the surgeon is able to perform a surgical procedure on the eyeball 26 on the assumption that the eyeball will remain fixed in place. For example, in the case of an automated disposable keratome, as noted above, a blade (not shown) may be activated to effect the slicing of a flap in the epithelial layer of the eyeball. Thereafter, use is made of a laser beam to ablate corneal tissue.

Typically, a low vacuum pressure, for example at 8" or less of mercury (Hg) is used to lock the eyepiece 25 to the eyeball. The locking effect takes place over milliseconds.

As tearing occurs during the surgical procedure, any fluid, i.e. salt water, emanating from the eyeball 26 into the end ring 27 via the ports 28 migrate down the inlet tube 14 and eventually into the fluid absorber 10. The compressed cellulosic sponge mass 12 of the absorber 10 will then absorb the fluid volume. For example, a typical surgical procedure will produce up to 0.5 cubic centimeters of fluid. The sponge mass 12 has a capacity of absorbing 1.5 cubic centimeters of fluid thereby providing an adequate safety factor while providing a minimal resistance to air flow so that the vacuum pump 26 is able to continue to operate at the vacuum pressure of 24 inches of mercury (Hg). Upon saturation of the compressed sponge mass 12, resistance to air flow increases slightly.

The capacity of the sponge mass 12 to absorb fluid without a significant increase in resistance to air flow allows a surgical procedure to continue under normal conditions. Typically, the amount of fluid to be adsorbed by the compressed sponge mass 12 is less than that which is reasonably expected during a surgical procedure.

The invention thus provides a disposable fluid absorber for absorbing a fluid volume within a suction tube set used with a keratome for laser eye surgery without significant increase in resistance to air flow.

The fluid absorber may be employed without regard to a vertical or horizontal disposition as the forces of gravity are not of any consequence in the functionality of the absorber.

While the sponge mass 12 has been described as a compressed cellulosic sponge mass, it is understood that other types of materials may also be used provided the materials satisfy the characteristic of absorbing an amount of fluid while increasing the resistance to air flow at saturation by only a small amount.

The suction tube set is characterized by having a low inherent pressure drop. When disconnected with the one end free and exposed to the room, the vacuum created at the entrance to the vacuum pump is approximately 7–8 inches of mercury. When connected to the eyepiece and there is no air leakage into the system, the vacuum pump will typically draw 26 inches plus of mercury.

A unique characteristic of this suction tube set is the ability to absorb quantities of a person's tears (salt water) with little change in resistance to air flow. Hence, after the fluid absorber has absorbed e.g. ½ cc of tears, the open line will still exhibit a vacuum of 8–10 inches of mercury.

This condition provides two advantages over suction lines containing filter traps which are generally the system of choice due to their inherent nature of positively preventing fluid from entering the vacuum pump and thereby destroying it's ability to continue to function. The first advantage is that the fluid absorber may absorb quantities of tears with minimal increase in resistance to air flow. The second advantage is the inherent low resistance to flow of the system.

The results of these advantages are the laser equipment can be programmed such that when resistance (negative pressure) at the vacuum pump inlet drops due to loss of suction at the connection between the eyeball 26 and suction ring 27, it will become immediately evident for a low vacuum pressure (below 15 inches of mercury) will instantaneously appear at the entrance to the vacuum pump. This pressure sensitivity can be translated into a signal which can inform the practitioner or when connected to the laser (surgical knife) will immediately shut the system down before harm can occur to the person's eye due to potential eye movement. (Improper cutting, cutting in the wrong area, etc.) The second advantage is that vacuum recovery when suction is lost due to leakage between the suction ring 27 and the eyeball 26 is significantly faster than suction systems using lower air flow due to higher line resistance. This reduces the likelihood of improper cutting or otherwise causing this medical procedure to result in poorer results than expected.

What is claimed is:

1. A fluid absorber for a suction tube set for a keratome, said fluid absorber comprising
    a hollow housing for connection at one side to a vacuum pump and for connection at an opposite side to a keratome; and
    a formed absorbent mass in said housing for absorbing a fluid without increasing the resistance to air flow at saturation by more than 3 inches of mercury.

2. A fluid absorber as set forth in claim 1 wherein said absorbent mass is a cellulosic sponge mass.

3. A fluid absorber as set forth in claim 2 wherein said housing has a first cap at one end with a spigot to receive a suction tube and a second cap/at the opposite end with a spigot to receive an inlet tube and which further comprises a first spacer tube between said sponge mass and said first cap and a second spacer tube between said sponge mass and said second cap.

4. A fluid absorber as set forth in claim 3 wherein said sponge mass is compressed by and between said spacer tubes.

5. A suction tube set comprising
    a hollowed housing of tubular shape;

a formed absorbent mass in said housing for absorbing a fluid whithout increasing the resistance to air flow at saturation by more than 3 inches of mercury;

a suction tube connected to one end of said housing for drawing a vacuum force within said housing; and an inlet tube connected to and extending from an opposite end of said housing for conveying a vacuum force therethrough.

6. A suction tube set as set forth in claim 5 wherein said absorbent mass is a compressed sponge mass.

7. A suction tube set as set forth in claim 6 wherein said compressed sponge mass is characterized in absorbing no more than 1.5 cubic centimeters of fluid.

8. A suction tube set as set forth in claim 6 wherein said compressed sponge mass is formed of a plurality of axially disposed layers.

9. A suction tube set as set forth in claim 7 wherein said housing has a first cap at one end with a spigot receiving said suction tube, and a second cap at an opposite end with a spigot receiving said inlet tube.

10. A suction tube set as set forth in claim 9 which further comprises a first spacer tube between said compressed sponge mass and said first cap and a second spacer tube between said compressed sponge mass and said second cap.

11. A suction tube set as set forth in claim 9 wherein said housing has a tubular barrel secured to and between said caps.

12. A suction tube set as set forth in claim 11 wherein said barrel is made of a thin transparent plastic.

13. A suction tube set as set forth in claim 5 wherein said mass is spaced from said first cap to define a gap therebetween and is spaced from said second cap to define a gap therebetween.

14. A suction tube set as set forth in claim 13 wherein said mass is secured in said housing at each of two opposite ends thereof to prevent movement of said mass within said housing against said end caps.

15. A suction tube set comprising a housing having a first spigot at one end and a second spigot at an opposite end;

a suction tube mounted on said first spigot of said housing to draw a suction force within said housing;

an inlet tube mounted on said second spigot of said housing to convey a suction force therethrough; and a formed absorbent mass in said housing for absorbing a fluid volume passing through said housing from said inlet tube without increasing the resistance to air flow at saturation by more than 3 inches of mercury.

16. A suction tube set as set forth in claim 15 wherein said formed absorbent mass has a capacity to absorb 1.5 cubic centimeters of fluid.

17. A suction tube set as set forth in claim 15 wherein said absorbent mass is formed of a plurality of coaxially disposed layers of compressed cellulosic sponge.

* * * * *